United States Patent
Strölin

(10) Patent No.: US 10,393,356 B2
(45) Date of Patent: Aug. 27, 2019

(54) SURGICAL LAMP WITH BRIGHTNESS REGULATION

(71) Applicant: KARL LEIBINGER MEDIZINTECHNIK GMBH & Co. KG, Mühlheim (DE)

(72) Inventor: Joachim Strölin, Rietheim (DE)

(73) Assignee: Karl Leibinger Medizintechik GmbH & Co. KG, Muehlheim (DE)

(*) Notice: Subject to any disclaimer, the term of this patent is extended or adjusted under 35 U.S.C. 154(b) by 0 days.

(21) Appl. No.: 15/751,920

(22) PCT Filed: Aug. 8, 2016

(86) PCT No.: PCT/EP2016/068893
§ 371 (c)(1),
(2) Date: Feb. 12, 2018

(87) PCT Pub. No.: WO2017/025513
PCT Pub. Date: Feb. 16, 2017

(65) Prior Publication Data
US 2018/0231227 A1    Aug. 16, 2018

(30) Foreign Application Priority Data
Aug. 13, 2015 (DE) .................. 10 2015 113 339

(51) Int. Cl.
*A61B 90/30* (2016.01)
*F21V 23/04* (2006.01)
(Continued)

(52) U.S. Cl.
CPC .......... *F21V 23/0464* (2013.01); *A61B 90/30* (2016.02); *F21V 23/0457* (2013.01);
(Continued)

(58) Field of Classification Search
CPC ............. F21V 23/0464; F21V 23/0457; H05B 37/0218; H05B 33/0854; A61B 90/30;
(Continued)

(56) References Cited

U.S. PATENT DOCUMENTS

| 5,068,767 A | 11/1991 | Koyama |
| 8,710,415 B2 | 4/2014 | Peyras |

(Continued)

FOREIGN PATENT DOCUMENTS

| DE | 10 202008018046 U1 | 6/2011 |
| DE | 10 2013 012 231 A1 | 1/2015 |

(Continued)

OTHER PUBLICATIONS

Office Action, DE 10 2015 113 339.3 (English translation included), dated Apr. 6, 2016 (13 pgs.).

(Continued)

*Primary Examiner* — Dedei K Hammond
*Assistant Examiner* — Raymond R Chai
(74) *Attorney, Agent, or Firm* — Eversheds Sutherland (US) LLP

(57) ABSTRACT

The invention relates to a surgical lamp for illuminating an operating area, including: a number of individual lamps which, in an activated state, form a light beam bundle generating a light field region in an illumination plane wherein a total light field is formed, a brightness detection device to determine an actual brightness value in the total light field, as well as a control unit which acts on the individual lamps such that the illumination intensity is controlled in accordance with the determined actual brightness value, wherein the brightness detection device and the control unit are designed such that an illumination intensity of a first individual lamp can be set in a targeted manner depending on the actual brightness value and same can be set (Continued)

for brightening or dimming a first light field region independently of an illumination intensity of a second individual light.

11 Claims, 2 Drawing Sheets

(51) Int. Cl.
    *H05B 33/08*     (2006.01)
    *H05B 37/02*     (2006.01)
    *F21Y 115/10*     (2016.01)
    *F21W 131/202*     (2006.01)
    *F21W 131/205*     (2006.01)

(52) U.S. Cl.
    CPC ..... *H05B 33/0854* (2013.01); *H05B 37/0218* (2013.01); *F21W 2131/202* (2013.01); *F21W 2131/205* (2013.01); *F21Y 2115/10* (2016.08)

(58) Field of Classification Search
    CPC .......... F21Y 2115/10; F21W 2131/205; F21W 2131/202
    See application file for complete search history.

(56) References Cited

U.S. PATENT DOCUMENTS

| | | | | |
|---|---|---|---|---|
| 2009/0318771 | A1* | 12/2009 | Marka | A61B 90/35 600/249 |
| 2009/0318772 | A1* | 12/2009 | Marka | A61B 90/35 600/249 |
| 2011/0037840 | A1 | 2/2011 | Hiltl et al. | |
| 2016/0317244 | A1* | 11/2016 | Jacobi | A61B 90/361 |

FOREIGN PATENT DOCUMENTS

| | | |
|---|---|---|
| EP | 2 136 126 A1 | 12/2009 |
| EP | 2 136 128 A1 | 12/2009 |
| EP | 2 283 790 B1 | 11/2010 |
| EP | 2 434 202 A1 | 3/2012 |

OTHER PUBLICATIONS

International Search Report and Written Opinion, dated Apr. 10, 2016 (13 pgs.).

* cited by examiner

SURGICAL LAMP WITH BRIGHTNESS REGULATION

TECHNICAL FIELD

Detailed Description

The invention relates to a surgical lamp for illuminating an operating area, comprising a plurality of individual lamps which, in an activated state, form a respective light beam bundle extending along a longitudinal axis and generating a light field region in an illumination plane, wherein the light field regions of the individual lamps are arranged next to one another and/or at least partially over one another (i.e. partially overlapping one another) in the illumination plane in such a way that a total light field (of the surgical lamp) is formed, comprising a brightness detection device which is designed to determine an actual brightness value in the total light field and comprising a control unit which acts on the individual lamps such that the illumination intensity is controlled in accordance with the actual brightness value determined by the brightness detection device (within a measuring area inside the total light field).

BACKGROUND OF THE INVENTION

From the state of the art generic surgical lamps are known already. For example, U.S. Pat. No. 8,710,415 B2 discloses an illumination device comprising a brightness regulation device for brightness regulation depending on the brightness of an illuminated field.

In the surgical lamps known from the state of the art it has turned out to be a drawback, however, that the total light fields thereof, when automatic brightness control is present, are relatively difficult to set individually to the specific operating region on a body to be operated on. This entails especially the drawback that during surgery also areas of a body to be operated on are brightened which actually should not be brightened as well. These are, for example, areas of the body that are brighter/more strongly reflecting such as skin areas, bones or fat tissue. By brightening said areas (due to an increase in illumination intensity) frequently the operating surgeon is dazzled. Concerning other darker areas, such as organs of the body that are darker or supplied more strongly with blood, which absorb much light and therefore reflect relatively few light beams, it is further required to facilitate more intense illumination/higher illumination intensity as compared to the brighter areas, for it is frequently relatively difficult for the operating surgeon to spot said dark areas. Thus, the prior art surgical lamps frequently entail the problem that the operating area is set to be locally either too bright or too dark, which may prevent the operating surgeon from correctly recognizing parts of the operating area of the body or may cause the operating surgeon to be strongly dazzled. It is also possible that, when the total light field is excessively illuminated, areas of the body to be operated on will dry out relatively quickly.

SUMMARY OF THE INVENTION

Therefore, it is the object of the present invention to eliminate the drawbacks known from the state of the art and, especially, to provide a surgical lamp which is intended to be adjustable in a most variable way to local situations within an operating area as regards the illumination thereof.

In accordance with the invention, this is achieved by the fact that the brightness detection device and the control unit are configured and the control unit is connected to the individual lamps such that, depending on the actual brightness value, an illumination intensity of a first individual lamp can be set in a targeted manner and independently of an illumination intensity of a second individual lamp for brightening or dimming a first light field region (formed by the first individual lamp).

This allows for controlling individual lamps separately/independently of each other as to their illumination intensity, thus enabling the total light field of the surgical lamp to be brightened or dimmed to a differently strong degree. This helps to adapt especially only those areas of the total light field as to their brightness for which such brightening is reasonable. For example, strongly reflecting areas thus can be also brightened less strongly or not at all, whereas dark areas absorbing much light can be significantly brightened. This allows for a more significant improvement of the operating surgeon's view onto the operating area.

Further advantageous embodiments are claimed in the subclaims and will be illustrated in detail hereinafter.

Accordingly, it is of particular advantage when the individual lamps are divided into plural lamp groups, with plural (first) individual lamps associated with a first lamp group being oriented and arranged relative to each other so that the longitudinal axes of the light beam bundles thereof intersect (in a common first intersection) in a first common focal plane.

In this context, it is further advantageous when plural (second) individual lamps associated with a second lamp group are oriented and arranged relative to each other so that the longitudinal axes of the light beam bundles thereof intersect (in a common (second) intersection) in a second focal plane arranged at a distance from the first focal plane. Consequently, also especially proper depth illumination is given by the surgical lamp.

When the control unit is connected electrically and/or by data transmission/transfer to the (first) individual lamps of the first lamp group and/or the (second) individual lamps of the second lamp group, the individual lamps within the lamp group can be equally controlled independently of each other such that the illumination intensity is set. Also, the individual lamps of the different groups may be controlled independently of each other. In this way, an especially versatile illumination intensity control/brightness control is realized so as to brighten the different individual operating areas always sufficiently strongly but not excessively.

It is also useful when the brightness detection device comprises at least one brightness sensor which includes at least one phototransistor, at least one photoresistor and/or at least one photodiode. This also helps to design an especially low-cost brightness detection device.

In this context, it is of particular advantage when the at least one brightness sensor is part of a (preferably medical) camera (photographic/video camera) of the brightness detection device. For in this way it is possible in an especially efficient manner to determine the brightness within a measuring range of the brightness detection device.

When, in addition, the brightness detection device detects at least one measuring area within the total light field, said measuring area having a smaller surface area than the total light field, the brightness detection device is always prevented from also detecting undesired areas outside the relevant operating area.

In this context, it is also especially advantageous when the brightness detection device determines the actual brightness value of the measuring area in total (i.e. integrally) or in part/in portions (in "spots"). This helps to determine the actual brightness values in an especially reliable manner.

It is further advantageous when each of the individual lamps during operation of the surgical lamp, i.e. in the activated state thereof, forms such light field areas that they are always overlapping/covering each other by a particular surface part with at least one further/adjacent light field area and a total light field covering/forming a coherent surface in a plane is resulting. In this way, an especially efficient illumination is realized.

When the brightness detection device further includes a camera, the brightness detection device may have an especially low-cost configuration.

Moreover, in this context it is of advantage when the camera includes a lens of fixed/fixedly set focal length. The focal length is selected, for example, so that the total light field is located in a plane of the focus of the lens. In this context, it is also especially advantageous when the total light field in a plane of the focus of the lens is larger than a measuring area optically detected by the camera in said plane. Thus, detection of the brightness can be performed especially efficiently, wherein the brightness measurement can be realized even in strongly brightened states/areas, as merely the exposure time has to be adapted.

For further facilitating the control of the camera, in another configuration a f-number (i.e. a transmission aperture of the lens leading to the sensor/brightness sensor of the camera) of the camera is defined/fixedly set (especially when an exposure time value of the camera can be set). Alternatively, said f-number of the camera is adjustable/variable (especially when an exposure time value of the camera is defined/fixedly set). This helps to especially easily automate the brightness measurement.

Thus, it is also useful when an exposure time value of the camera is or can be fixedly set, which equally allows implementation of a brightness measurement to be more efficient.

When the brightness detection device comprises a luminance meter or when the brightness detection device is in the form of such luminance meter, with the afore-described camera preferably being in the form of a luminance meter in that case, the brightness can be detected especially accurately.

Moreover, it is also useful when the brightness detection device is inserted/installed/positioned/integrated in a lamp receiving member receiving the individual lamps or is inserted/installed/positioned/integrated in a handle device detachably connectable to the lamp receiving member. Thus, no additional space is required for the brightness detection device and the surgical lamp can be substantially designed without any additional installation space.

It is of particular advantage in this context, when each individual lamp is defined/configured by including a single lamp, preferably an LED lamp that is integrated in a lamp unit/lamp module along with an optical lens system. This allows to control the individual lamps in an especially easy manner.

When the brightness detection device detects the actual brightness value continuously/permanently, in intervals or after manual input of a recording command by an actuating unit connected to the control unit, the brightness can be adapted in an especially variable manner.

Advantageously, the brightness detection device is also configured so that it fades out areas at a particular distance from the lamp receiving member, for example at least 50 cm away from the lamp receiving member by measurement technique. This will always ensure that an element not directly disturbing/covering the illumination plane is prevented from being inadvertently wrongly illuminated.

Furthermore, the invention also relates to a method of controlling such surgical lamp according to at least one of the afore-described embodiments for illuminating an operating area, the surgical lamp comprising a plurality of individual lamps forming, in an activated state, a respective light beam bundle extending along a longitudinal axis and generating a light field region in an illumination plane, wherein the light field regions of the individual lamps are arranged next to one other and/or at least partially over one another in the illumination plane such that a total light field is formed; a brightness detection device which is designed to determine an actual brightness value in the total light field, and a control unit which acts on the individual lamps such that the illumination intensity is controlled in accordance with the determined actual brightness value, wherein the brightness detection device and the control unit are designed in such way that and the control unit is connected to the individual lamps in such way that an illumination intensity of a first individual lamp can be set in a targeted manner depending on the actual brightness value and can be set for brightening or dimming a first light field region independently of an illumination intensity of a second individual lamp.

BRIEF DESCRIPTION OF THE DRAWINGS

Hereinafter the invention shall be illustrated in detail by way of Figures in which also different embodiments are described, wherein.

The Figures are merely schematic and serve exclusively for the comprehension of the invention. Like elements are provided with like reference numerals.

Figure 2:
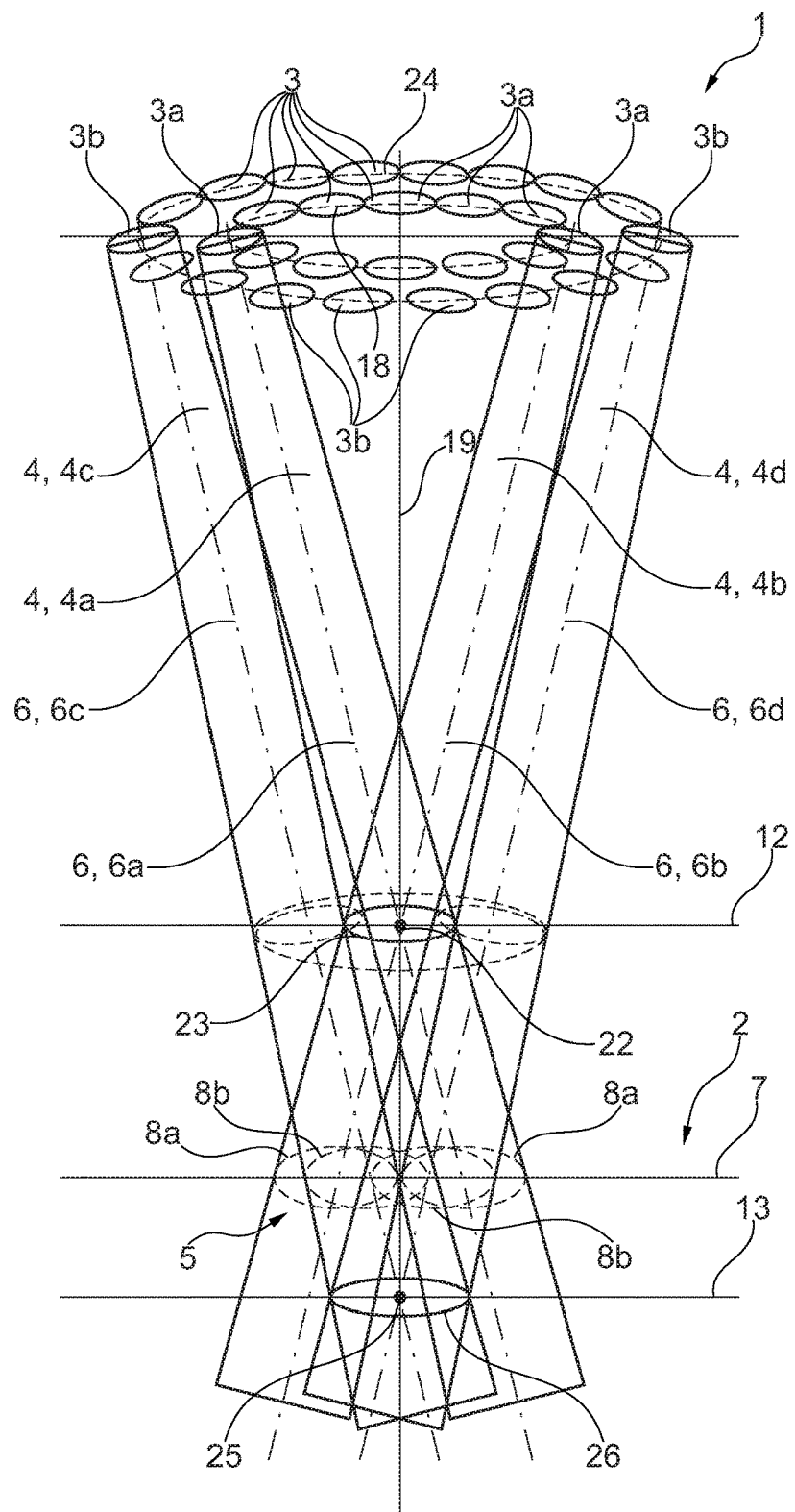
FIG. 2 shows a schematic representation of the surgical lamp according to FIG. 1, wherein the division of the plurality of individual lamps contained in the surgical lamp into different lamp groups is especially clearly visible.

The surgical lamp 1 according to the invention is especially clearly visible in FIG. 2 as to its schematic structure. The surgical lamp 1 in the usual way serves for illuminating/lighting an operating area 2 of an object, such as a person, lying on a treatment table.

The surgical lamp 1 includes a plurality of individual lamps hereinafter referred to as individual lamps 3. Each individual lamp 3 consists of a single lamp module, i.e. materially formed individually/separately from the other individual lamps 3. The lamp module in turn comprises a LED lamp/bulb/LED light and a pertinent lens/optical lens system. Each of the individual lamps 3 always includes only one LED in its lamp module. Moreover, each lamp module has appropriate reflectors or devices for bundling the light emitted by the LED which light exits the lamp module on the side of the lens in the form of a light beam bundle 4. Thus, each individual lamp 3 forms a light beam bundle 4 extending along a longitudinal axis 6 when being activated/supplied with current. In other words, each individual lamp 3 and, resp., each lamp module of the individual lamp 3 produces a light beam bundle 4.

In FIG. 2, for a schematic representation of the orientation of the individual lamps 3 two first individual lamps 3a associated with a first lamp group 11a/lens group are activated. Further, two second individual lamps 3b associated with a second lamp group 11b/lens group are activated.

The first lamp group 11a in this configuration consists not only of two but of more than two first individual lamps 3a. In total, in the first lamp group 11a twelve of the first individual lamps 3a are contained. In further configurations, the number of the first individual lamps 3a of the first lamp group 11a also amounts to more than twelve or to less than twelve.

The first individual lamps 3a of the first lamp group 11a are arranged along a ring-shaped/circular ring-shaped peripheral line, hereinafter referred to as first peripheral line 18. The first peripheral line 18 is arranged centrically with respect to an imaginary central axis 19 of the surgical lamp 1. The central axis 19 of the surgical lamp 1 during operation forms the central axis 19 of a lamp receiving member 16 of the surgical lamp 1 which is not shown in detail in FIG. 2 for reasons of clarity but is schematically evident in FIG. 1. The lamp receiving member 16 is the member on which the plurality of single individual lamps 3 (comprising first individual lamps 3a and second individual lamps 3b) is received/fastened. Consequently, all of the individual lamps 3 are fastened on said lamp receiving member 16. Furthermore, the central axis 19 also is the axis which is provided in the center of the lamp receiving member 16 of the surgical lamp 1 and substantially extends along a handle device 17 (FIG. 1) of the surgical lamp 1. Especially, the central axis 19 is the axis along which a journal-type grip portion 21 of the handle device 17 hereinafter being described in detail which can be touched by the operating surgeon is extending.

Thus, the first individual lamps 3a of the first lamp group 11a are arranged/stringed next to one another (in chain structure). All of the first individual lamps 3a are oriented at an angle relative to the central axis 19 so that all of the longitudinal axes 6 thereof (the longitudinal axes 6 are those axes along which the light beam 4 is extending) intersect in a common intersection, here referred to as first intersection 22 located in a common first focal plane 12. Therefore, all of the longitudinal axes 6 of the first individual lamps 3a form the same angle with the central axis 19. From the lamp module of the individual lamps 3a the respective light beam 4 therefore extends toward the central axis 19 so that the common focal point/intersection—first intersection 22—forms in the first focal plane 12. Since all of the first individual lamps 3a of the first lamp group 11a in their activated state intersect/overlap/cover each other in said common first intersection 22 located in the first focal plane 12, they form a common first round focal light field 23 in said first focal plane 12. The individual first light field regions 8a generated by each of the first individual lamps 3a thus are completely overlapping in said first focal plane 12, while the one circular/common first focal light field 23 is formed. The first focal light field 23 has a maximum first diameter of approx. 300 mm.

In FIG. 2, schematically two first individual lamps 3a opposite to each other with respect to the central axis 19 are activated so that one of the first individual lamps 3a produces a first light beam bundle 4a extending along a first longitudinal axis 6a and another first individual lamp 3a arranged to be offset by about 180° along the first peripheral line 10 forms a second light beam bundle 4b extending along a second longitudinal axis 6b. Up to the first section 22 the two light beam bundles 4a, 4b extend toward each other and from a side of the first focal plane 12 facing away from the surgical lamp 1 said two light beam bundles 4a, 4b then in turn extend away from each other, when viewed at the same angle (with respect to the angular amount) of the respective longitudinal axis 6a, 6b with the central axis 19 in each case.

In an illumination plane arranged at a distance from the first focal plane 12, here the illumination plane 7, each of the light beam bundles 4a and 4b of the two first individual lamps 3a forms/illuminates a separate light field region 8.

As is further evident in interaction with FIG. 2, apart from the first group/lamp group 11a of the first individual lamps 3a a second lamp group 11b/lens group is provided which, in turn, includes plural single lamps, i.e. plural individual lamps 3, said individual lamps pertinent to the second lamp group 11b hereinafter being referred to as second individual lamps 3b. The second individual lamps 3b of the second lamp group 11b have the same structure and function as the first individual lamps 3a. Thus, also each of the second individual lamps 3b has a lamp module including only one LED and one lens/optical lens system associated with said LED.

The second individual lamps 3b of the second lamp group 11b are arranged radially outside of the first individual lamps 3a of the first lamp group 11a, when viewed relative to the central axis 19. The second individual lamps 3b, too, are arranged circularly next to one another on a peripheral line hereinafter referred to as second peripheral line 24. Thus, also the second individual lamps 3b are arranged in the peripheral direction of the central axis 19. The second peripheral line 24 consequently has a larger diameter than the first peripheral line 18.

Also, in the second lamp group 11b again not only two (second) individual lamps 3b but more than two (second) individual lamps 2b are used. In total, eighteen second individual lamps 2b are contained in the second lamp group 11b and are stringed to one another in chain structure along the circular second peripheral line 14. However, in further configurations also a different number of second individual lamps 3b is realized in the second lamp group 11b, such as more than eighteen or less than eighteen. In addition, it is referred to the fact that it is not mandatory for each of the individual lamps 3; 3a and 3b to have a circular arrangement extending along a circular peripheral line 18, 24. It is also imaginable to differently arrange the individual lamps 3a, 3b of the lamp groups 11a, 11b relative to each other without deviating from the inventive idea.

All of the second individual lamps 3b again are oriented from the lamp receiving member 16 toward the central axis 19. All of the second individual lamps 3b in turn enclose, with their longitudinal axes 6 of the light beam bundles 4, an angle with the central axis 19. The longitudinal axes 6 of all of the second individual lamps 3b in this case form the same angle with the central axis 19.

In FIG. 2, schematically also two second individual lamps 3b are activated which are opposite to each other substantially by 180° with respect to the second peripheral line 24. Either of the two second individual lamps 3b produces a light beam bundle 4 referred to as third light beam bundle 4c extending along the third longitudinal axis 6c. The other of the two second individual lamps 3b in turn produces a fourth light beam bundle 4d extending along a fourth longitudinal axis 6d. The two second individual lamps 3b are adapted to each other so that their longitudinal axes 6c and 6d intersect in a common focal point/intersection—hereinafter referred to as second intersection 25. Said second intersection 25 is located in a second focal plane 13 arranged at a distance vis-à-vis relative to the first focal plane 12. Furthermore, not only the longitudinal axes 6c, 6d of the two second individual lamps 3b activated in FIG. 2 but all second individual lamps 2b contained in the second lamp group 11b do intersect with their longitudinal axes 6 in said common second intersection 25 in the second focal plane 13. Since all of the second individual lamps 3b of the second lamp group 11b in their activated state intersect/overlap/cover each other in said common second intersection 25, they form a common second round focal light field 26 in said second focal plane 13. The individual second light field regions 8b produced by each of the second individual lamps 3b thus are completely overlapping in said second focal plane 13 while forming the one circular/common second focal light field 26. The second focal light field 26 has a maximum second diameter of approx. 150 mm. In the illumination plane 7 arranged at a distance from the second focal plane 12 each of the light beam bundles 4c and 4d of the two second individual lamps 3b illuminates a separate light field region 8b.

Each focal plane 12 and, resp., 13 in this configuration is designed as a normal plane relative to the central axis 11, i.e. the central axis 19 is oriented normal to both focal planes 12, 13 (arranged in parallel to each other). The first focal plane 12 is arranged, when viewed along the central axis 19, more closely to the surgical lamp 1, i.e. to the lamp receiving member 16 of the surgical lamp 1 than the second focal plane 13. Therefore, the first focal plane 12 has a smaller distance along the central axis 19 relative to the surgical lamp 1 than the second focal plane 13. In an especially advantageous embodiment, the distance of the first focal plane 12 along the central axis 19 from the surgical lamp 1/from the lamp receiving member 16 amounts to 1 m and the distance of the second focal plane 13 along the central axis 19 relative to the surgical lamp 1/to the lamp receiving member 16 amounts to 1.20 m, especially preferred to 1.40 m.

The individual lamps 3a, 3b in this configuration form elliptic light field regions 8a, 8b. In another embodiment, the light field regions 8a, 8b are partly angled, such as diamond-shaped.

In a schematically shown illumination plane 7 provided (when viewed in the axial direction of the central axis 19) between the two focal planes 12, 13 in this embodiment, due to the distance of the illumination plane 7 from the focal planes 12, 13 all of the individual lamps 3a, 3b of both lamp groups 11a, 11 b form a respective light field region 8. The two first individual lamps 3a activated in FIG. 2 in the illumination plane 7 generate the first light field region 8a, while each of the activated second individual lamps 3b in turn generates a second light field region 8b. The light field regions 8a and 8b are partially mutually overlapping, i.e. covering each other. For example, the second light field region 8b of either of the second individual lamps 3b covers all other light field regions 8a, 8b of the further first and second individual lamps 3a, 3b.

Thus, a total light field 5 of the individual lamps 3a, 3b controlled in FIG. 2 is produced by combination of the individual light field regions 8a, 8b. Depending on the first and/or second individual lamps 3a, 3b which are supplied with current, the total light field 5 thus can be formed in different light field arrays/light field geometries, with the light field geometry 27 (i.e. the geometry of the total light field 5) in this example being linearly formed, wherein the individual light field regions 8a, 8b of the individual lamps 3a, 3b are linearly stringed to one another (with mutual partial overlapping).

The individual lamps 3a and 3b of the first lamp group 11a and of the second lamp group 11b as well as all further individual lamps 3, if present, can be supplied with current, i.e. can be electrically controlled/actuated independently of each other within the lamp group 11a, 11b as well as between the lamp groups 11a, 11b so that the produced total light field 5 can be geometrically adjusted in any way in the illumination plane 7. An adjustment of the light field geometry 27 can be understood to be both a variation of the shape and, resp., the proportions of the total light field 5 (i.e. of the individual light field regions 8; 8a, 8b) and a variation of the orientation of the total light field 5 (i.e. of the light field geometry 18) inside the illumination plane 7.

Figure 1:
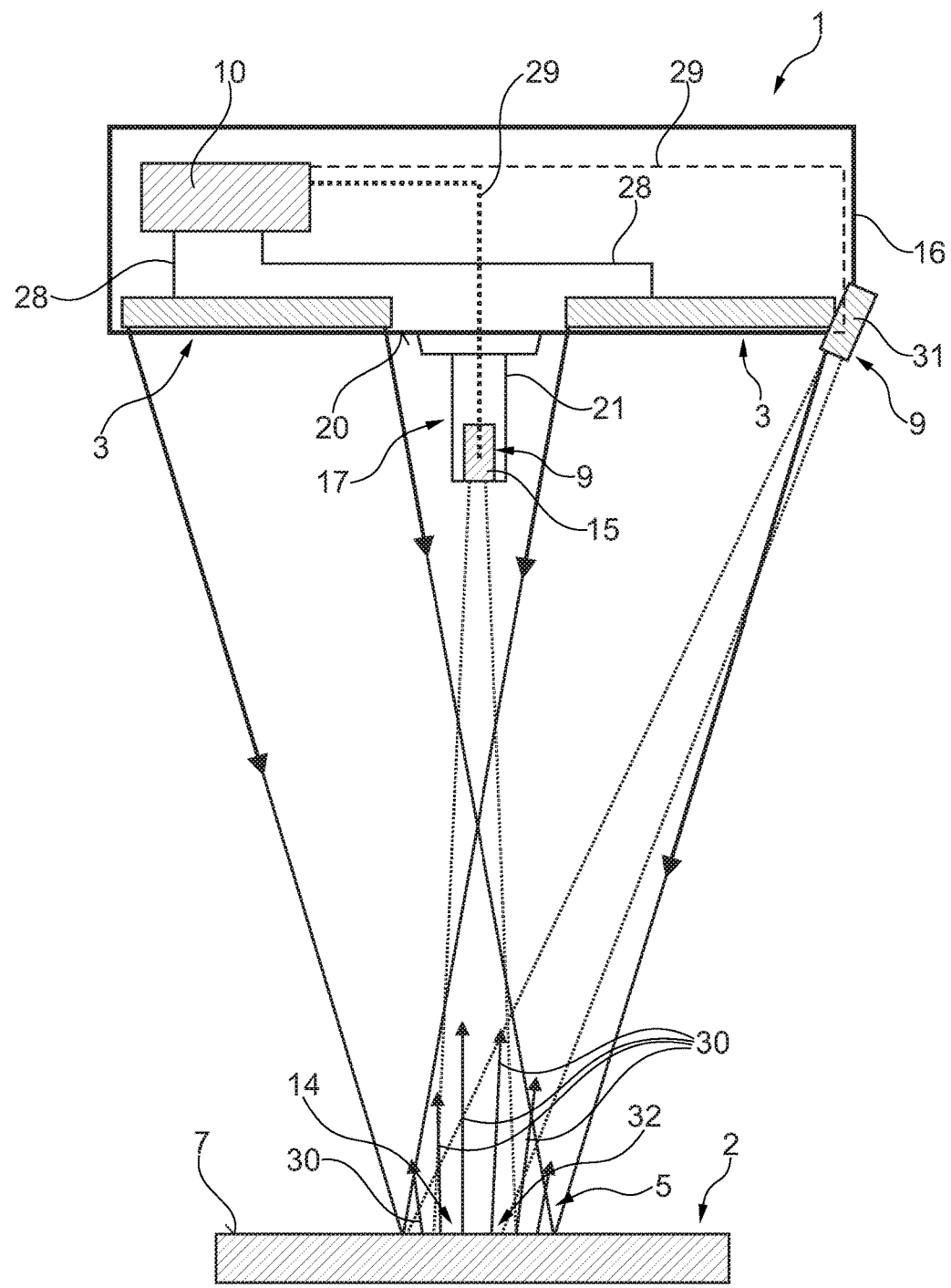
FIG. 1 shows a schematic view of a surgical lamp of the type according to the invention, wherein a lamp receiving member of the surgical lamp is illustrated in partial section and a brightness detection device of the surgical lamp is integrated within a handle device detachably fastened to the lamp receiving member of the surgical lamp.

For controlling the individual lamps 3; 3a, 3b a control unit 10 is further integrated/contained in the surgical lamp 1, viz. in the lamp receiving member 16 of the surgical lamp 1. The internal structure of the surgical lamp 1 and of the lamp receiving member 16 is especially clearly evident from FIG. 1. In FIG. 1, the particular individual lamps 3a, 3b are not shown individually any more, but are schematically indicated in a simplified form by depicted blocks. Also, the electric connection between the individual lamps 3a, 3b and the control unit 10 is indicated merely schematically by means of two electric lines 28.

In this configuration, although not shown in detail for reasons of clarity, the control unit 10 is connected electrically as well as for data transmission to each lamp group 11a, 11b and especially to each particular individual lamp 3a, 3b of the lamp groups 11a, 11b. This connection ensures that the control unit 10 individually supplies the individual lamps 3a, 3b with current and, resp., activates and deactivates the same as required in response to a generated control command. The control unit 10 is further connected to a brightness detection device 9. The control unit 10 is connected to the brightness detection device 9 by means of wireless data transmission/data communication 29 in the form of radio communication.

The brightness detection device 9 is the device that is configured for measuring/determining the brightness in the total light field 5. During operation of the surgical lamp 1, the control unit 10 is permanently connected to the brightness detection device 9 via the data transmission 29 so that data are transferred. The brightness values determined/measured by the brightness detection device 9 within a measuring area 14 of the total light field 5, hereinafter referred to as actual brightness values, then are transmitted to the control unit 10 via the data transmission 29. The control unit 10 is configured so that—in response to the at least one actual brightness value determined by the brightness detection device 9—it acts on the respective individual lamps 3a, 3b so as to control, viz. so as to control the illumination intensity. The control unit 10 acts on the individual lamps 3a, 3b independently of the remaining individual lamps 3a, 3b. Thus, according to the invention, the brightness detection device 9 as well as the control unit 10 are designed in such a way and the control unit 10 is connected, according to the invention, to the individual lamps 3; 3a, 3b in such a way (i.e. the control unit 10 acts on the individual lamps 3 so as to control the same) that, depending on the at least one actual brightness value, the illumination intensity of a first individual lamp 3a can be set in a targeted manner for brightening or dimming (i.e. for varying the brightness of) the first light field region 8a independently of the illumination intensity of one of the second individual lamps 3b.

For this purpose, the brightness detection device 9 is oriented such that a measuring area 14 determined by the brightness detection device 9 is always arranged within the total light field 5 so that it is ensured that only a measuring area 14 which is relevant to the illumination of the illumination plane 7 is detected.

The brightness detection device 9 includes a camera 15 for measuring/recording the measuring area 14, hereinafter also referred to as first camera 15. The camera 15 usually comprises a lens/an optical system as well as a measuring sensor in the form of a brightness sensor/light sensor, which is not shown in detail here for the sake of clarity. However, the brightness sensor per se need not be integrated within a camera 15, as designed here. In further configurations, the brightness sensor is configured without any lens and thus is provided as a loose brightness sensor and is integrated in the lamp receiving member 16. The brightness sensor in this configuration includes plural phototransistors, wherein, alternatively, it may as well be a photoresistor or a photodiode or a group of photoresistors or of photodiodes.

As is further especially clearly evident from FIG. 1, the orientation of the camera 15, especially of the lens thereof, defines the position of the measuring area 14. In this design, the first camera 15 is arranged inside the handle device 17, i.e. the camera 15 is integrated in the handle device 17. The handle device 17 is the device that is tightly connected to the lamp receiving member 16 during operation of the surgical lamp 1. By arranging the individual lamps 3 in a fixed orientation on the lamp receiving member 16 it is possible to set the surgical lamp 1 including the lamp receiving member 16 during operation/in the operating phase by touching the handle device 17 and by applying a particular adjusting force. The handle device 17 including its handle portion 21, which has a substantially tubular design, is detachably disposed on the lamp receiving member 16. In this way, the handle device 17 can be easily sterilized as the whole. The camera 15 is inserted/accommodated inside the tubular/hollow handle portion 21. The handle portion 21 extends substantially along the central axis 19, i.e. normal to an imaginary fastening plane 20 on the lamp receiving member 16. On a side facing away from the lamp receiving member 16 the handle portion 21 is recessed, i.e. it includes an opening so that the camera 15 may detect, by its lens, the measuring area 14 on the illumination plane 7. Thus, the camera 15 is equally oriented along said central axis 19.

Moreover, the camera 15 is configured so that it includes a fixed lens/a fixed optical system having a fixed/fixedly set focal length. The first camera 15 can be set as to its exposure time so that it always measures reliably plural actual brightness values depending on the total brightness of the measuring area 14. As it is schematically represented here by means of the return beams 30, a particular part of the light originally emitted (by the light beams 4) from the individual lamps 3a, 3b is reflected and is measured/determined/detected/recorded by the camera 15.

In addition, the camera has a fixed/fixedly set f-number so that automatic readjustment takes place corresponding to the exposure time value so as to constantly reach the fixedly set f-number. As an alternative, in another configuration the camera 15 is also configured in such way that, instead of the fixedly set f-number, it has a variable f-number and instead the exposure time is fixed, i.e. fixedly set. In this way, the automatic iris function of the camera 15 is used for exposure measurement. Thus, only one value of the camera 15 has to be set at a time so as to produce a reliable image of the measuring area 14.

By way of the image of the measuring area 14 taken by the camera 15, by evaluating the individual detected pixel brightness values by the control unit 10 plural actual brightness values associated with at least a subarea of the measuring area 14 at a time are detected/determined, which actual brightness values contribute to the total brightness of the measuring area 14. Depending on the brightness of the individual subareas of the measuring area 14, the illumination intensity of the individual lamp 3a, 3b illuminating the respective subarea with its light field region 8a, 8b is readjusted/adapted.

Thus, the camera 15 is designed so that in this configuration it simultaneously detects the measuring area 14 and associates plural actual brightness values (one actual brightness value for each subarea) with the measuring area 14/image area/image divided into plural subareas/partial surfaces. The measuring area 14 of the camera 15 consequently is divided into plural spot ranges, i.e. spots, according to which then the different actual brightness values of the different subareas of the measuring area 14 are determined. As an alternative, it is also possible, however, to integrally detect the measuring area 14 and to determine one single actual brightness value from said measuring area 14. In such case, preferably plural cameras 15 are provided, each recording one measuring area 14 and transmitting one actual brightness value to the control unit 10.

Within the control unit 10 in turn different logarithms are deposited according to which the control unit 10 acts on the individual lamps 3a, 3b which help to form the total light field 5 by their light beam bundles 4 such that the illumination intensity is controlled in accordance with the determined actual brightness values, so as to adjust the illumination intensity thereof. If, for example, the camera 15 detects a too bright actual brightness value in a subarea of the measuring area 14, the individual lamp 3a, 3b or the plural individual lamps 3a, 3b which help to illuminate the subarea of the measuring area 14 is/are appropriately dimmed, i.e. the illumination intensity thereof is reduced. In contrast to this, with a too dark brightness value the control unit 10 acts in such way that the respective subarea of the measuring area 14 then in turn brightens the individual lamps 3 independently of each other, i.e. increases the illumination intensity thereof.

In this embodiment, the brightness detection device 9 comprises not only the first camera 15 but also a second camera 31 which in turn has the same design and function as the first camera 15, however. This second camera 31, too, is connected to the control unit 10 by means of data transmission 29. However, the second camera 31 is not integrated within the detachable handle device 17 but is attached to/in the lamp receiving member 16. In this design, the second camera 31 is positioned at a radial outside of the lamp receiving member 16, when viewed with respect to the central axis 19. The second camera 31 is not oriented with its field of view in parallel to or, as the first camera 15, coaxially with the central axis 19, but is oriented so that its lens is inclined relative to the central axis 19. In this way, the second camera 32 records a somewhat larger (second) measuring area 32 than the first camera 15. The measuring area of the second camera will hereinafter be referred to as second measuring area 32. The two cameras 15 and 31 are oriented so that the measuring areas 14 thereof are arranged to be offset against each other. I.e. the two measuring areas 14 and 32 are not congruent but are substantially offset against each other. This allows recording, by means of the second camera 31, a further measuring area 32 arranged independently of the first measuring area 14 but again within the total light field 5. The second camera 31, too, in turn detects the reflection 30.

For the sake of completeness, it is further mentioned that the two cameras 15, 31 or else at least the first camera 15 or the second camera 31 may be formed individually as luminance meters, thus allowing the brightness detection device 9 to work even more efficiently.

Furthermore, the brightness detection device 9, viz. the respective camera 15, 31, continuously/permanently detects the actual brightness values, i.e. by plural pictures per second. As an alternative, it is also possible that either the first camera 15 or the second camera 31 or both cameras 15 and 31 detect the measuring areas 14 and 32 thereof at intervals, for example at recording intervals of plural seconds or minutes between the individual pictures or, further alternatively, by manual input of a recording command at an actuating device. This allows the cameras 15, 31 to work even more efficiently.

In other words, it is thus possible to evaluate the aperture function of a camera 15, 31 and thus to realize a regulating function. Moreover, sensors and measuring devices can be used by which also the luminance and, resp., the brightness of a surface of the illumination plane 7 can be measured. According to the invention, the light intensity is automatically adapted to the operating area/operating field, i.e. to the illumination plane 7. The automatic light intensity/brightness regulation has a gentle effect on the operating area, as unnecessary radiation is prevented from reaching the operating area and any drying effect due to the heating is prevented from occurring. In addition, eye-friendly and fatigue-free work of the operating surgeon is realized by the fact that substantially no glare will occur and unnecessary high illumination intensities will be avoided.

Accordingly, the image information of the camera 15, 31 or of an appropriate sensor is evaluated. By way of auto iris control (exposure measurement) of the camera 15, 31 focused on the operating area, the light intensity thus can be readjusted and can be set to an appropriate value by the appropriate lamp electronics and the surgical lamp 1. Contactless measurement of the brightness and, resp., of the reflective radiation in the operating area is thus possible. The brightness can be set by means of the luminance meter or the light sensor/photodiode/phototransistor/photoresistor measuring the reflected light radiation of the illuminated object surface. Readjustment of the light intensity/luminance of the surgical lamp 1 then is carried out to an appropriate value. Said system may as well be adjusted by manual setting of the maximum illumination intensity at which glare will not yet occur e.g. on white underground. Upon changing to the automatic system, said illumination intensity is taken as a reference and glare is also avoided on different undergrounds.

When the surgical lamp 1 is equipped with a medical camera 15, 31 for imaging, the f-numbers can be automatically read out and used directly for regulating the brightness. The f-number may be determined as a spot or integral. It is also imaginable to determine image recognition of the brightest spot (the glare) and consequently to evaluate the same for correction. When, on the other hand, the surgical lamp 1 is not equipped with a camera 15, 31 for imaging, a sensor or a very low-cost camera may fulfil this function. It is also imaginable that this function continuously influences dimming. This might entail problems, however, e.g. when light-colored surgical gloves are used and thus the light conditions are continuously varying. Therefore, it would be imaginable to avoid this with an adjustment being realized at appropriate time intervals. Moreover, manual triggering of the measurement, e.g. at the central sterilizable handle/handle device would be imaginable. For this purpose, ideally the view onto the operating area is cleared so as to then trigger measurement. Accordingly, the lamp 1 will automatically adjust its brightness to the current situation.

REFERENCE NUMERALS

1 Surgical lamp
2 operating area
3 individual lamp
3*a* first individual lamp
3*b* second individual lamp
4 light beam bundle
4*a* first light beam bundle
4*b* second light beam bundle
4*c* third light beam bundle
4*d* fourth light beam bundle
5 total light field
6 longitudinal axis
6*a* first longitudinal axis
6*b* second longitudinal axis
6*c* third longitudinal axis
6*d* fourth longitudinal axis
7 illumination plane
8 light field region
8*a* first light field region
8*b* second light field region
9 brightness detection device
10 control unit
11*a* first lamp group
11*b* second lamp group
12 first focal plane
13 second focal plane
14 measuring area
15 camera/first camera
16 lamp receiving member
17 handle device
18 first peripheral line
19 central axis
20 fastening plane
21 handle portion
22 first intersection
23 first focal light field
24 second peripheral line
25 second intersection
26 second focal light field
27 light field geometry
28 line
29 data transmission
30 return beam/reflection
31 second camera
32 second measuring area It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

I claim:

1. A surgical lamp for illuminating an operating area, comprising
a plurality of individual lamps of a plurality of lamp groups which, in an activated state, form a respective light beam bundle extending along a longitudinal axis and generating a light field region in an illumination plane, wherein the light field regions of the individual lamps are arranged next to one another and/or at least partially over one another in the illumination plane in such way that a total light field is formed, and wherein plural individual lamps associated with a first lamp group are oriented and arranged relative to one another so that the longitudinal axes of the light beam bundles thereof intersect in a first common focal plane and plural individual lamps associated with a second lamp group are oriented and arranged relative to each other so that the longitudinal axes of the light beam bundles thereof intersect in a second common focal plane arranged at a distance from the first focal plane, a brightness detection device which is designed to determine an actual brightness value in the total light field, as well as a control unit which acts on the individual lamps such that the illumination intensity is controlled in accordance with the determined actual brightness value, wherein the brightness detection device and the control unit are designed in such a way that the control unit is connected to the individual lamps such that an illumination intensity of a first individual lamp of the first lamp group is adjustable in a targeted manner depending on the actual brightness value and is adjustable for brightening or dimming a first light field region independently of an illumination intensity of a second individual lamp of the first lamp group, wherein the brightness detection device includes a camera, wherein the camera includes a lens having a fixedly set focal length.

2. The surgical lamp according to claim 1, wherein the control unit is electrically connected to the individual lamps of the first lamp group and/or to the individual lamps of the second lamp group.

3. The surgical lamp according to claim 1, wherein the brightness detection device comprises at least one brightness sensor including at least one phototransistor, at least one photoresistor and/or at least one photodiode.

4. The surgical lamp according to claim 1, wherein the brightness detection device detects at least one measuring area within the total light field, which measuring area has a smaller surface area than the total light field.

5. The surgical lamp according to claim 4, wherein the brightness detection device determines the actual brightness value of the measuring area-in total or in part.

6. The surgical lamp according to claim 1, wherein a f-number of the camera is fixedly set or settable.

7. The surgical lamp according to claim 1, wherein an exposure time value of the camera is fixedly set or settable.

8. The surgical lamp according to claim 1, wherein the brightness detection device comprises a luminance meter or the brightness detection device is in the form of the luminance meter.

9. The surgical lamp according to claim 1, wherein the brightness detection device is inserted in a lamp receiving member receiving the individual lamps or is integrated in a handle device adapted to be detachably connected to the lamp receiving member.

10. The surgical lamp according to claim 1, wherein the brightness detection device detects the actual brightness value continuously, at intervals or upon manual input of a recording command.

11. A method for controlling a surgical lamp for illuminating an operating area, with the surgical lamp, comprising a plurality of individual lamps of a plurality of lamp groups which, in an activated state, form a respective light beam bundle extending along a longitudinal axis and generating a light field region in an illumination plane, wherein the light field regions of the individual lamps are arranged next to one another and/or at least partially over one another in the illumination plane in such way that a total light field is formed, and wherein plural individual lamps associated with a first lamp group are oriented and arranged relative to one another so that the longitudinal axes of the light beam bundles thereof intersect in a first common focal plane and plural individual lamps associated with a second lamp group are oriented and arranged relative to each other so that the longitudinal axes of the light beam bundles thereof intersect in a second common focal plane arranged at a distance from the first focal plane, a brightness detection device which is designed to determine an actual brightness value in the total light field, wherein the brightness detection device includes a camera and the camera includes a lens having a fixedly set focal length, as well as a control unit which acts on the individual lamps such that the illumination intensity is controlled in accordance with the determined actual brightness value, wherein the brightness detection device and the control unit are designed in such a way that the control unit is connected to the individual lamps such that an illumination intensity of a first individual lamp of the first lamp group is set in a targeted manner depending on the actual brightness value and is set for brightening or dimming a first light field region independently of an illumination intensity of a second individual lamp of the first lamp group.

* * * * *